US00PP11133P

United States Patent [19]

Churchus

[11] Patent Number: Plant 11,133

[45] Date of Patent: Nov. 23, 1999

[54] LYSIMACHIA PLANT NAMED 'GOLDEN HARVEST'

[75] Inventor: John William Churchus, Devon Meadows, Australia

[73] Assignee: Plants Management Australia Pty. Ltd., Warragul, Australia

[21] Appl. No.: 09/048,060

[22] Filed: Mar. 26, 1998

[51] Int. Cl.[6] ..... A01H 5/00

[52] U.S. Cl. ..... Plt./263

[58] Field of Search ..... Plt./263

*Primary Examiner*—Howard J. Locker

*Assistant Examiner*—Kent L. Bell

*Attorney, Agent, or Firm*—C. A. Whealy

[57] ABSTRACT

A new and distinct cultivar of Lysimachia plant named 'Golden Harvest', characterized by its compact and prostrate spreading plant habit; greenish gold with reddish toned young leaves and greenish gold to green to yellowish green mature leaves; numerous bright yellow flowers; long flowering period; and tolerance to high and low temperatures.

1 Drawing Sheet

BACKGROUND OF THE INVENTION

The present invention relates to a new and distinct variety of Lysimachia plant, botanically known as *Lysimachia congestiflora*, and hereinafter referred to by the name 'Golden Harvest'.

The new cultivar was discovered by the inventor in Devon Meadows, Victoria, Australia, as a naturally-occurring mutation of the *Lysimachia congestiflora* 'Outback Sunset' (U.S. Plant Patent application Ser. No. 08/726,423, now abandoned) and was observed in a group of plants of the parent cultivar in 1993. The selection of this plant was based on its compactness and leaf color.

Asexual reproduction of the new cultivar by terminal cuttings taken at Devon Meadows, Victoria, Australia, has shown that the unique features of the new Lysimachia are stable and reproduced true to type in successive generations of asexual reproduction.

BRIEF SUMMARY OF THE INVENTION

The following traits have been repeatedly observed and are determined to be the unique characteristics of 'Golden Harvest'. These characteristics in combination distinguish the new Lysimachia as a new and distinct cultivar:

1. Compact and prostrate spreading plant habit.
2. Young leaves greenish gold with reddish tones, mature leaves greenish gold to green to yellowish green.
3. Numerous bright yellow flowers.
4. Long flowering period.
5. Tolerance to high and low temperatures.

In side-by-side comparisons conducted in Devon Meadows, Victoria, Australia, and Keller, Tex., plants of the new Lysimachia differ from plants of the parent variety, *Lysimachia congestiflora* 'Outback Sunset', in the following characteristics:

1. Plants of the new Lysimachia have solid yellow to yellowish green leaves whereas plants of 'Outback Sunset' have random green markings across the leaf.
2. Plants of the new Lysimachia are more compact and more outwardly spreading than plants of 'Outback Sunset'.
3. Plants of the new Lysimachia are more floriferous than plants of 'Outback Sunset'.

The new Lysimachia has not been observed under all possible environmental conditions. The phenotype may vary significantly with variations in environment such as temperature and light level, without, however, any variance in genotype.

BRIEF DESCRIPTION OF THE PHOTOGRAPHS

The accompanying colored photographs illustrate the overall appearance and flower color of the new Lysimachia, showing the colors as true as it is reasonably possible to obtain in colored reproductions of this type.

The photograph at the top of the sheet comprises a top perspective view of a typical plant of the new Lysimachia.

The photograph at the bottom of the sheet comprises a close-up view of typical leaves and flowers of the new Lysimachia. Flower and foliage colors in the photographs may appear different from the actual colors due to light reflectance.

DETAILED BOTANICAL DESCRIPTION

The following observations, measurements, values, and comparisons describe plants grown under outdoor production conditions in 15-cm containers in Keller, Tex., in full sun and partial shade during the summer.

In the following description, color references are made to The Royal Horticultural Society Colour Chart except where general terms of ordinary dictionary significance are used.

Botanical classification: *Lysimachia congestiflora* 'Golden Harvest'.

Parentage: Naturally-occurring mutation of *Lysimachia congestiflora* 'Outback Sunset'.

Propagation:

*Method.*—By terminal cuttings or by tissue culture.

*Time to initiate roots.*—Summer: About 5 days at a temperature of 25° C. Winter: About 7 days at a temperature of 15° C.

*Time to develop roots.*—Summer: About 15 days at a temperature of 25° C. Winter: About 25 days at a temperature of 15° C.

*Rooting habit.*—Numerous, fibrous, and freely-branching.

Plant description:

*Form.*—Initially upright, then horizontally spreading to prostrate herbaceous plant. Freely branching, dense growth. Numerous bright yellow flowers that face outward and upright.

*Usage*.—Suitable for 10 to 20-cm containers; recommended for hanging baskets and patio containers; excellent garden performance. Tolerant to low and high temperatures.

*Vigor*.—Vigorous and rapid growth rate.

*Plant height*.—About 17 cm.

*Plant spread*.—About 50 cm.

*Branching habit*.—Freely branching with lateral branches forming at every node, pinching will enhance branching, branches strong and flexible.

*Stem description*.—Lateral branch diameter: About 3 mm. Internode length: About 2.75 cm. Texture: Fine white pubescence. Color: Young: Close to 182A. Mature: 145A to 145C.

*Foliage description*.—Leaves simple, generally symmetrical, abundant, opposite, and flat in aspect. Length: About 6 cm. Width: About 3.7 cm. Shape: Ovate with acute to acuminate apex, obtuse base and entire margin. Texture: Slightly pubescent on both surfaces, fleshy. Color: Young leaves, upper surface: Greenish gold, close to 153A/153B, with reddish, close to 178A, tones and margin. Reddish tones decrease with development. Young leaves, lower surface: Greener than 160A with reddish, close to 178A, tones and margin. Fully expanded leaves, upper surface: Greenish gold, close to 153A/153B, to green, 152C, to greener than 144A/144B to yellowish green, 151A. Fully expanded leaves, lower surface: Close to 146B/146C/146D to yellowish green, close to 151A. Petiole: Length: About 1.4 cm. Diameter: About 3.5 mm. Color: Upper surface: 144B. Lower surface: Close to 145B.

Flower description:

*Flower type and habit*.—Typical of *Lysimachia congestiflora*, star-shaped flowers typically five-parted occasionally six-parted, fused at base, and axillary. Usually three to five flowers per axil. Freely and continuously flowering. Flowers face outward and upright. Flowers last about one week.

*Flowering season*.—Flowering generally occurs spring throughout summer.

*Flower diameter*.—About 1.75 cm.

*Flower depth*.—About 1.7 cm.

*Petals*.—Length: About 1 cm. Width: About 6.5 mm. Shape: Obovate with rounded to acute apex and entire margin. Texture: Satiny, smooth. Color: When opening, upper surface: 9A. Mature, upper surface: 9A. Mature, lower surface: 9C.

*Sepals*.—Arrangement: Five fused at base. Shape: Linear/elongate with acute apex and entire margin. Calyx length: About 6 mm. Calyx diameter: About 2 mm. Texture: Pubescent. Color: 145A with reddish margin.

*Peduncles*.—Length: About 3 mm. Angle: Erect and upright. Strength: Flexible. Color: Light green with reddish tones.

*Reproductive organs*.—Androecium: Stamen number: Five, fused at base. Anther shape: Oblong. Anther length: About 1 mm. Amount of pollen: Moderate. Pollen color: Golden orange. Gynoecium: Pistil length: About 6.5 mm. Stigma shape: Rounded. Stigma color: Light green. Style color: Yellowish green.

Seed development: Seed development has not been observed on plants of the new Lysimachia.

Disease resistance: Under commercial conditions, plants of the new Lysimachia have not been observed to be more or less resistant to fungal pathogens common to Lysimachia than other known cultivars of Lysimachia.

It is claimed:

1. A new and distinct Lysimachia plant named 'Golden Harvest', as illustrated and described.

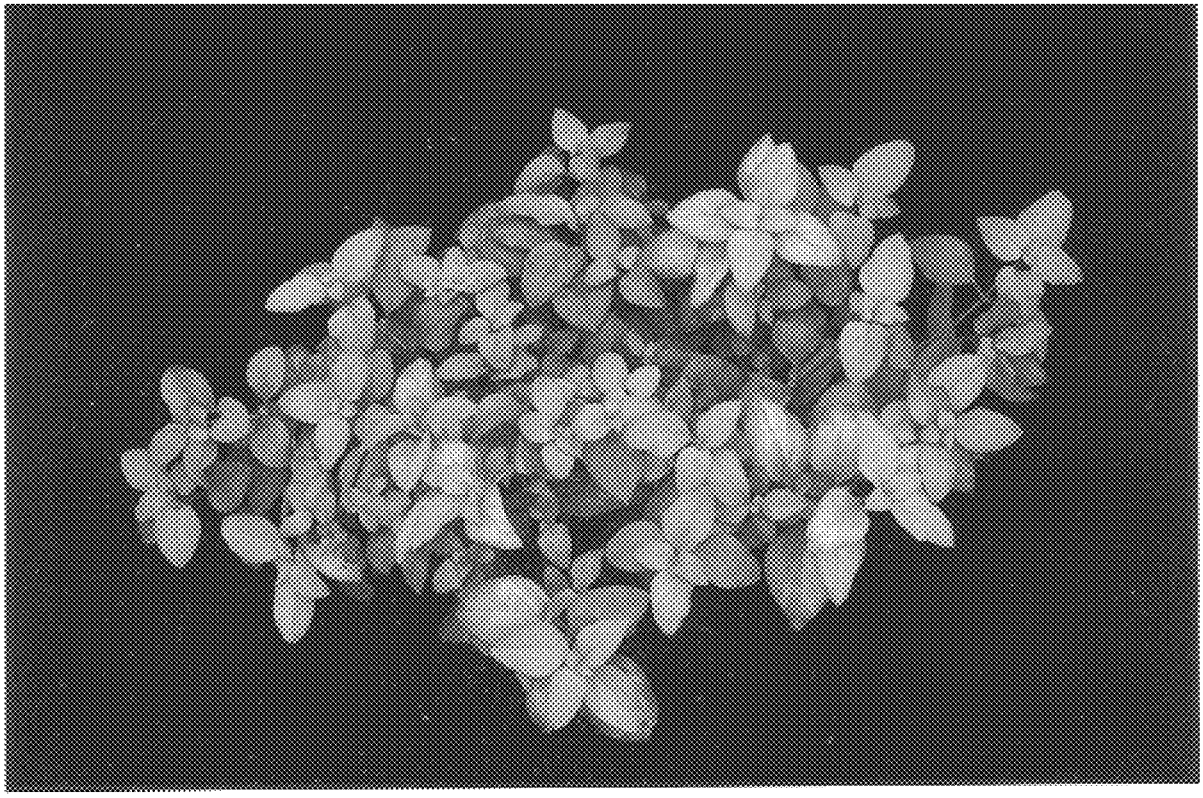
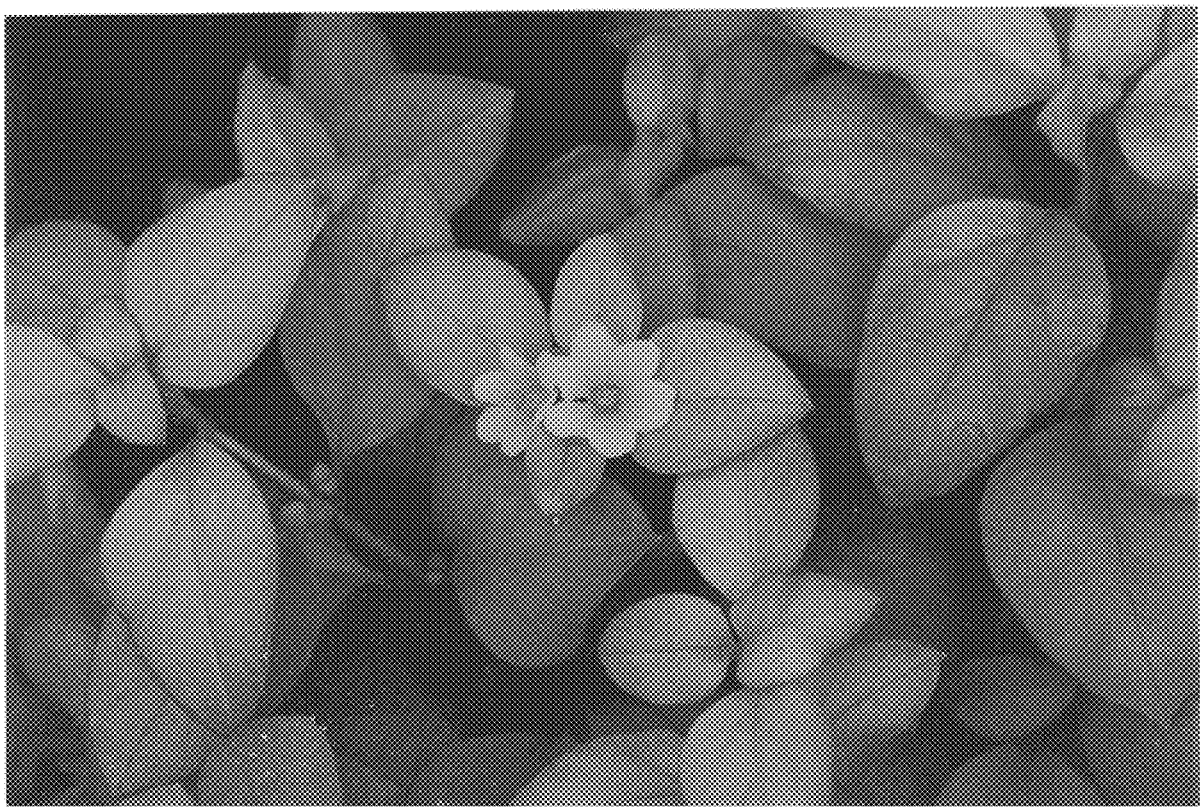

* * * * *